(12) United States Patent
Yamamoto et al.

(10) Patent No.: US 7,084,982 B2
(45) Date of Patent: Aug. 1, 2006

(54) OPTICAL APPARATUS, MEASUREMENT METHOD, AND SEMICONDUCTOR DEVICE MANUFACTURING METHOD

(75) Inventors: Takeshi Yamamoto, Tochigi (JP); Akira Miyake, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 422 days.

(21) Appl. No.: 10/626,744

(22) Filed: Jul. 25, 2003

(65) Prior Publication Data
US 2004/0156052 A1  Aug. 12, 2004

(30) Foreign Application Priority Data
Jul. 25, 2002  (JP)  ............................. 2002-216938

(51) Int. Cl.
*G01N 21/47* (2006.01)
(52) U.S. Cl. ...................................... 356/446
(58) Field of Classification Search ..................... None
See application file for complete search history.

(56) References Cited

U.S. PATENT DOCUMENTS

| 6,825,481 | B1 * | 11/2004 | Miyake | 250/492.2 |
| 6,864,490 | B1 * | 3/2005 | Underwood et al. | 250/461.1 |
| 6,867,843 | B1 * | 3/2005 | Ogushi et al. | 355/30 |
| 2003/0090662 | A1 | 5/2003 | Yamamoto | 356/401 |
| 2005/0006600 | A1 * | 1/2005 | Shichi et al. | 250/492.21 |

* cited by examiner

*Primary Examiner*—Gregory J. Toatley, Jr.
*Assistant Examiner*—Ali Allawi
(74) *Attorney, Agent, or Firm*—Fitzpatrick, Cella, Harper & Scinto

(57) ABSTRACT

An optical apparatus includes an optical device arranged on an optical path extending from a light source to a predetermined position, an optical sensor, and a measuring device which measures an optical characteristic or a change in an optical characteristic of the optical device on the basis of an output from the optical sensor. The optical sensor is arranged outside the optical path and senses light which is emitted from a second light source arranged outside the optical path and is reflected by the optical device.

25 Claims, 13 Drawing Sheets

OPTICAL APPARATUS, MEASUREMENT METHOD, AND SEMICONDUCTOR DEVICE MANUFACTURING METHOD

FIELD OF THE INVENTION

The present invention relates to an optical apparatus, a measurement method, and a semiconductor device manufacturing method.

BACKGROUND OF THE INVENTION

FIG. 11 shows an example of an exposure apparatus, which exposes a substrate, such as a wafer, or the like, to a pattern. In FIG. 11, exposure light 102 emitted from a laser oscillator 101 as an exposure light source is guided to a wafer 111 placed on a wafer stage 112 through reflection mirrors 103 and 108, relay lenses 106 and 107, a reticle 109, and a projection optical system 110.

Conventionally, to measure a change in reflectance of the reflection mirror 103, exposure is temporarily stopped, and an intensity monitor 104 attached to a retractable mechanism 105 is inserted to an optical path, thereby performing measurement.

For this reason, while the reflectance of an optical device, such as the reflection mirror 103 is measured, the wafer 111 cannot be exposed to a pattern.

SUMMARY OF THE INVENTION

The present invention has been made in consideration of the above-mentioned problem, and has as its exemplified object to measure in situ an optical characteristic or its change of an optical device arranged on an optical path.

According to the first aspect of the present invention, there is provided an optical apparatus comprising an optical device arranged on an optical path extending from a light source to a predetermined position, an optical sensor, and a measuring device which measures an optical characteristic or a change in optical characteristic of the optical device on the basis of an output from the optical sensor, wherein the optical sensor is arranged outside the optical path.

According to a preferred embodiment of the present invention, the optical sensor preferably senses light scattered by the optical device.

According to a preferred embodiment of the present invention, the optical sensor senses scattered light scattered by a substance generated from the light source and deposited on the optical device.

According to a preferred embodiment of the present invention, preferably, the apparatus further comprises a second optical sensor arranged outside the optical path to sense light directly incident from the light source, and the measuring device measures the optical characteristic or the change in optical characteristic of the optical device on the basis of an output from the second optical sensor in addition to the output from the optical sensor.

According to a preferred embodiment of the present invention, the optical sensor preferably senses light which is emitted from a second light source arranged outside the optical path and is reflected by the optical device.

According to a preferred embodiment of the present invention, the optical sensor preferably senses light which is emitted from a second light source arranged outside the optical path and is scattered by the optical device.

According to a preferred embodiment of the present invention, the optical sensor senses light which is emitted from a second light source arranged outside the optical path and is scattered by a substance generated from the light source, and is deposited on the optical device.

According to a preferred embodiment of the present invention, preferably, the apparatus further comprises a second light sensor arranged outside the optical path to sense light, the optical sensor senses light which is emitted from a second light source arranged outside the optical path and is reflected by the optical device, the second optical sensor senses light which is emitted from the second light source and is scattered by the optical device, and the measuring device measures the optical characteristic or the change in optical characteristic of the optical device on the basis of an output from the second optical sensor in addition to the output from the optical sensor.

According to a preferred embodiment of the present invention, preferably, the apparatus further comprises a memory which stores information indicating a correlation between the optical characteristic or the change in optical characteristic of the optical device and a detection or measurement result of light which is emitted from the second light source and is reflected by the optical device, and the measuring device measures the optical characteristic or the change in optical characteristic of the optical device on the basis of the output from the optical sensor and the correlation.

According to a preferred embodiment of the present invention, preferably, the apparatus further comprises a memory which stores information indicating a correlation between the optical characteristic or the change in optical characteristic of the optical device and a detection or measurement result of light which is emitted from the second light source and is scattered by the optical device, and the measuring device measures the optical characteristic or the change in optical characteristic of the optical device on the basis of the output from the second optical sensor and the correlation.

According to the second aspect of the present invention, an optical apparatus comprises an optical device arranged on an optical path extending from a light source to a predetermined position, a deposition amount sensor, and a measuring device which measures a deposition amount of a substance generated from the light source and deposited on the optical device on the basis of an output from the deposition amount sensor, wherein the deposition amount sensor is arranged outside the optical path.

According to a preferred embodiment of the present invention, preferably, the apparatus further comprises a memory which stores information indicating a correlation between the optical characteristic or the change in optical characteristic of the optical device and the deposition amount of the substance deposited on the optical device, and the measuring device derives the optical characteristic or the change in optical characteristic of the optical device on the basis of an output from the deposition amount sensor and the correlation.

According to a preferred embodiment of the present invention, preferably, the optical sensor senses light which is emitted from a second light source arranged outside the optical path and passes through the optical device.

According to a preferred embodiment of the present invention, preferably, the apparatus further comprises a second light sensor arranged outside the optical path to sense light, the optical sensor senses light which is emitted from a second light source arranged outside the optical path and is scattered by the optical device, the second optical sensor senses light which is emitted from the second light source and passes through the optical device, and the measuring device measures the optical characteristic or the change in optical characteristic of the optical device on the basis of an output from the second optical sensor in addition to the output from the optical sensor.

According to a preferred embodiment of the present invention, the light source preferably comprises an EUV light source.

According to a preferred embodiment of the present invention, the EUV light source is a laser plasma light source.

According to a preferred embodiment of the present invention, the optical characteristic is reflectance.

According to a preferred embodiment of the present invention, preferably, the apparatus further comprises a projection optical system for projecting a pattern onto a substrate and is configured as an exposure apparatus.

According to the third aspect of the present invention, there is provided a measurement method comprising steps of measuring an optical characteristic or a change in optical characteristic of an optical device arranged on an optical path extending from a light source to a predetermined position, on the basis of an output from an optical sensor arranged outside the optical path.

According to the fourth aspect of the present invention, there is provided a semiconductor device manufacturing method comprising steps of coating a substrate with a photosensitive agent, transferring a pattern onto the substrate coated with the photosensitive agent in the coating step using an optical apparatus as defined above, and developing the photosensitive agent on the substrate bearing the pattern transferred in the exposure step.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DETAILED DESCRIPTION OF THE PREFERRED EMBODIMENTS

Optical apparatuses according to preferred embodiments of the present invention will be described below with reference to FIGS. 1 to 10.

Figure 10:
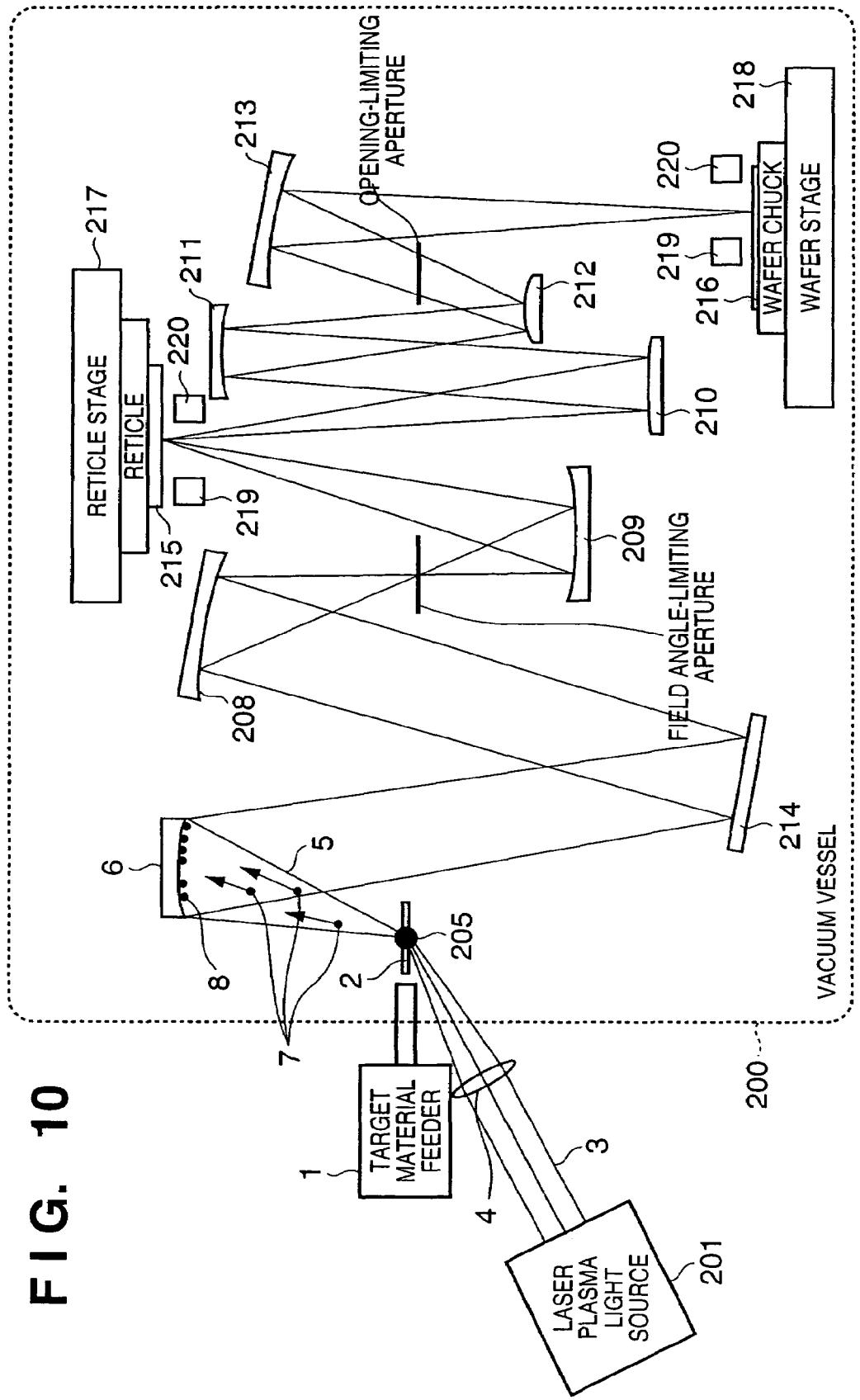
FIG. 10 is a view showing the concept of an EUV exposure apparatus as an example of an optical apparatus according to still another preferred embodiment of the present invention.
Figure 11:
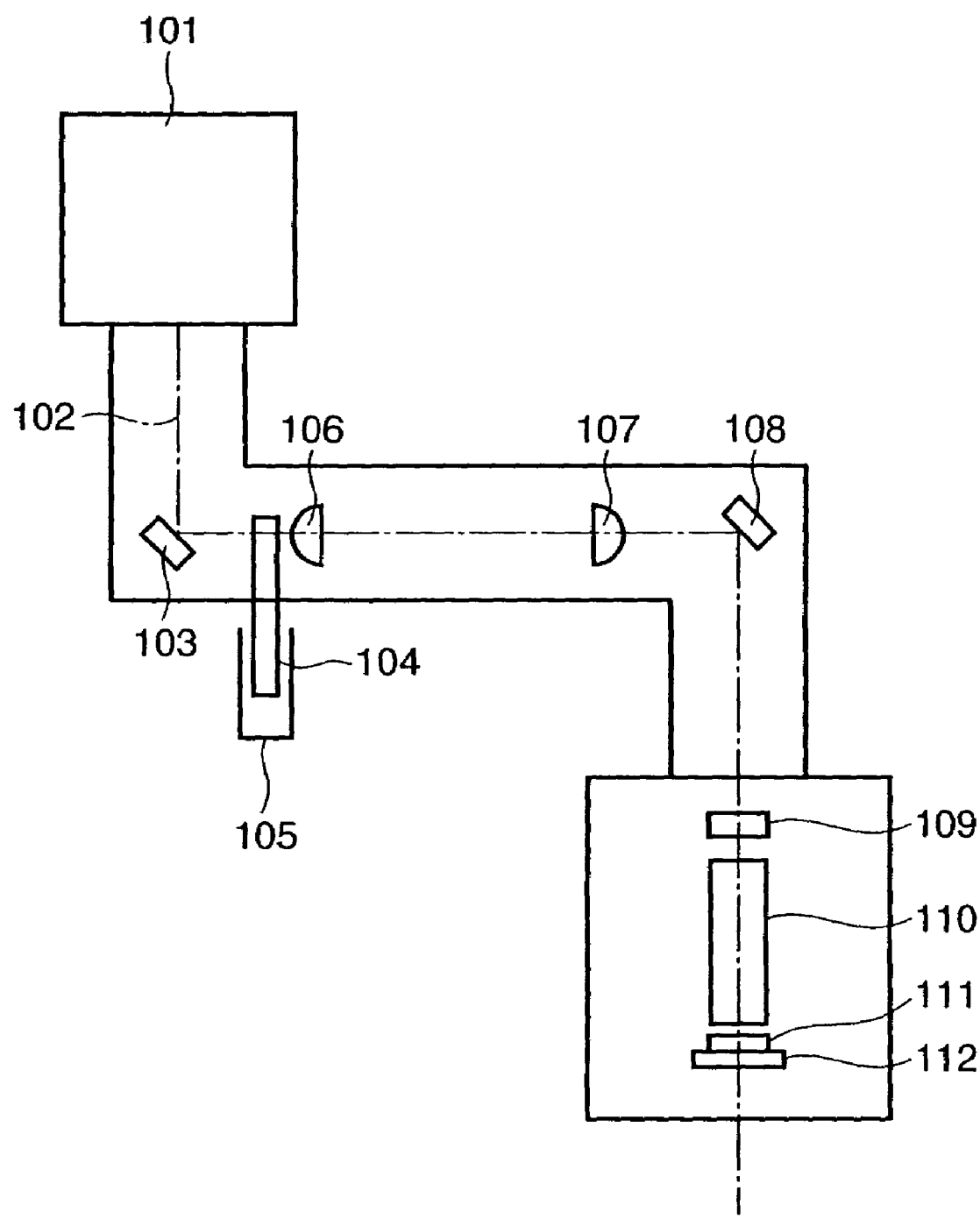
FIG. 11 is a view showing an example of an exposure apparatus which exposes a wafer to a pattern.

FIG. 10 is a view showing the concept of an EUV exposure apparatus as an example of an optical apparatus according to a preferred embodiment of the present invention. The EUV exposure apparatus will be explained while comparing it with a conventional exposure apparatus.

Reduction projection exposure using, for example, ultraviolet rays is conventionally performed as a pattern transfer method (lithography) in manufacturing a semiconductor device bearing a fine pattern, such as a semiconductor memory, logic circuit, or the like.

The minimum size of a pattern which can be transferred by reduction projection exposure is proportional to the wavelength of light for use in the transfer and inversely proportional to the numerical aperture of a projection optical system. For this reason, to transfer a finer circuit pattern, the wavelength of light for use in the transfer is decreasing, and the wavelength of ultraviolet rays for use with a mercury-vapor lamp i-line (wavelength: 365 nm), a KrF excimer laser beam (wavelength: 248 nm), and an ArF excimer laser beam (wavelength: 193 nm) is decreasing.

However, semiconductor devices and the like are rapidly being miniaturized, and this miniaturization is hard to realize by lithography using ultraviolet light. Under the circumstances, to efficiently transfer a very fine circuit pattern with a line width of, e.g., below 0.1 µm, a reduction projection exposure apparatus, as shown in FIG. 10, using extreme ultraviolet light (EUV light) with a wavelength (about 10 to 15 µm) shorter than those of ultraviolet rays is being developed.

In FIG. 10, e.g., a laser plasma light source 201 is employed as an EUV light source. The laser plasma light source 201 condenses high-intensity pumping pulse laser beams 3 by a condenser lens 4 and irradiates a target material 2 placed in a vacuum vessel 200 with the beams to generate a high-temperature plasma 205. The laser plasma light source 201 utilizes EUV light 5 (whose wavelength is, e.g., about 13 nm) emitted from the light source of the plasma 205. A metal thin film, inert gas, droplets, or the like, is adopted as the target material 2. The target material 2 is supplied into the vacuum vessel 200 by a gas jet, or the like. To increase the average intensity of the EUV light 5 emitted from the light source of the plasma 205, the repetition frequency of the pumping pulse laser beams 3 is preferably high. The pumping laser is generally operated at a repetition frequency of several kHz. To efficiently utilize the EUV light 5 emitted from the light source of the plasma 205, a condenser mirror is provided. Optical devices used to induce total reflection, such as a focusing mirror, include, e.g., a multilayer mirror formed by stacking about 20 layer pairs each consisting of Mo and Si films.

The illumination optical system includes a plurality of multilayer mirrors or obliquely incident mirrors (e.g., a first illumination system mirror 6, a second illumination system mirror 208, and a third illumination system mirror 209 in FIG. 10), an optical integrator 214, and the like. The optical integrator 214 is used to uniformly illuminate a mask at a predetermined numerical aperture.

The EUV light 5 supplied from the illumination optical system is reflected by a reticle 215 serving as a master and is reduced to about ¼ by a projection optical system including four to six multilayer mirrors (e.g., a first projection system mirror 210, a second projection system mirror 211, a third projection system mirror 212, and a fourth projection system mirror 213 in FIG. 10) to irradiate a resist-coated wafer 216. The reticle 215 and wafer 216 are held by a reticle stage 217 and a wafer stage 218, respectively. Alignment detection optical systems 219 precisely align the reticle 215 and wafer 216, and the reticle 215 and wafer 216 are precisely focused by focus detection optical systems 220. The EUV exposure apparatus has a mechanism of scanning, in this state, on the wafer 216, in synchronism with the reticle stage 217 at a velocity ratio proportional to the reduction magnification. In a state wherein a reduced projected image of the reticle 215 is formed on the wafer 216, the operation of scanning the reticle 215 and wafer 216 in synchronism with each other is repeated (step and scan). In this manner, the pattern of the reticle 215 is transferred onto the entire surface of the wafer 216.

The laser plasma light source 201 as a type of light source of the EUV light 5 irradiates the target material 2 supplied from a target material feeder 1 with the high-intensity pumping pulse laser beams 3, thereby generating the EUV light 5. At the same time, the laser plasma light source 201 generates scattered particles referred to as debris 7 and 8. As a result, the debris 7 and 8 contaminate and damage an optical device (e.g., the first illumination system mirror 6), thereby causing a change in optical characteristic (e.g., a decrease in reflectance).

Optical apparatuses according to preferred embodiments of the present invention will be described next.

FIGS. 1 to 9 are views focusing on the target material feeder 1, target material 2, pumping pulse laser beams 3, condenser lens 4, EUV light 5, first illumination system mirror 6, and debris 7 (especially, the debris 8 deposited on the mirror surface) in FIG. 10. Note that the same reference numerals as those in FIGS. 1 to 9 denote the same elements.

First Embodiments

Figure 1:
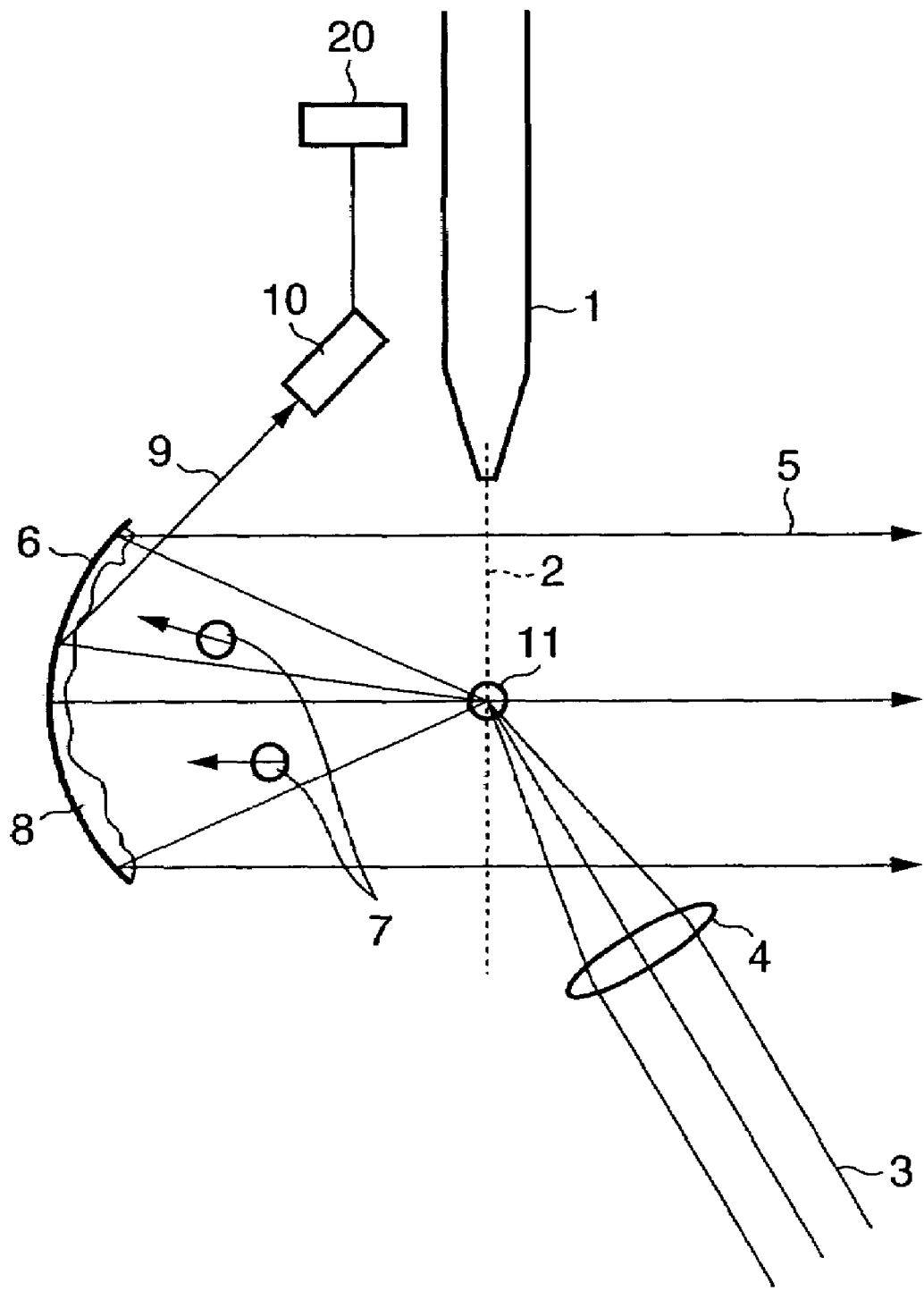
FIG. 1 is a schematic view showing an optical apparatus according to the first embodiment of the present invention.

FIG. 1 is a schematic view showing an optical apparatus according to the preferred first embodiment of the present invention.

The target material 2 discharged from the target material feeder 1 is irradiated with the pumping pulse laser beams 3 condensed by the condenser lens 4, thereby generating a plasma light source 11. The optical device, which is located on an optical path (of the EUV light 5) from the plasma light source 11 to a predetermined position (e.g., an object to be exposed), reflects the EUV light 5 emitted from the plasma light source 11 in a downstream direction of the optical path. At this time, scattered particles referred to as the other debris 7 are generated and deposited on the surface of the optical device 6 (reference numeral 8 in FIG. 1 denotes debris deposited on the optical device).

In FIG. 1, a sensor 10, which detects scattered light 9, which is generated when light emitted from the plasma light source 11 is scattered by the optical device 6, is arranged outside the optical path of the EUV light 5. The sensor 10 is arranged at a position different from that of the optical path of the EUV light 5 reflected by the optical device 6 (i.e., a position which will block the optical path concerned in exposure). A measuring device 20 measures an optical characteristic or its change of the optical device 6 on the basis of the measurement result of the scattered light 9 obtained by the sensor 10. The optical characteristics of the optical device 6 include the light reflectance of the optical device 6. Since the sensor 10 is not arranged on the optical path of the EUV light 5, it will not block the EUV light 5. For this reason, while the optical apparatus is performing an exposure operation (an example of an operation which cannot be executed when the optical path is blocked), an optical characteristic or its change of the optical device 6 can constantly be measured. More specifically, this optical apparatus can measure in situ the optical characteristic or its change of the optical device 6 on the optical path.

Second Embodiment

Figure 2:
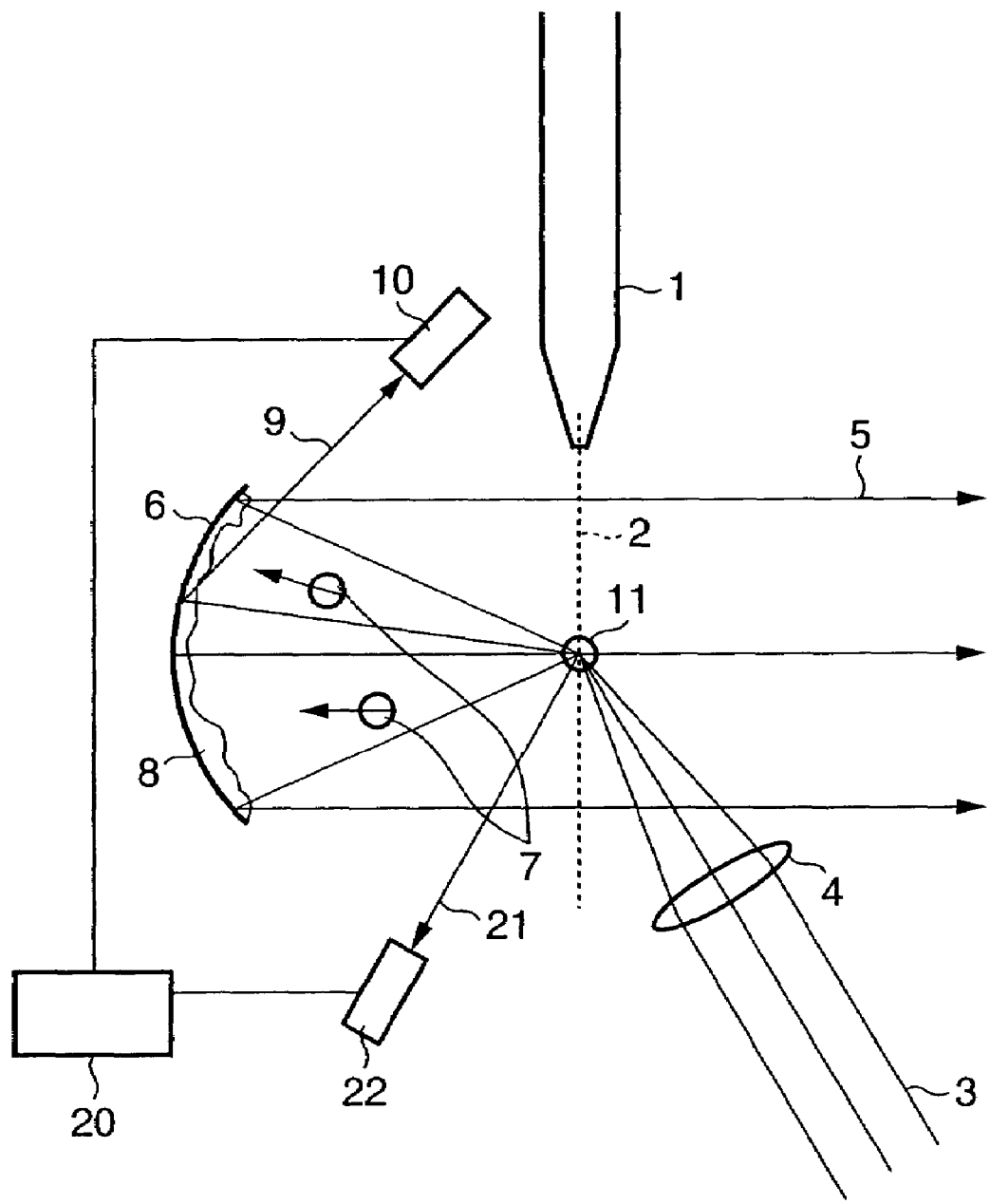
FIG. 2 is a schematic view showing an optical apparatus according to the second embodiment of the present invention.

FIG. 2 is a schematic view showing an optical apparatus according to the preferred second embodiment of the present invention. In addition to the components of FIG. 1, a sensor 22, which detects direct incident light 21 directly emitted from a plasma light source 11, is arranged outside the optical path of the EUV light 5. A measuring device 20, which measures an optical characteristic or its change of the optical device 6 by comparing the measurement result of the direct incident light 21 with that of scattered light 9 from the optical device 6, is provided in place of the measuring device of FIG. 1. The measuring device 20 of the second embodiment can sense the optical characteristic or its change of the optical device 6 by sensing the magnitude of the scattered light 9 relative to that of the direct incident light 21.

The plasma light source 11 emits the EUV light 5 substantially uniformly and radially to its surroundings. For this reason, the sensor 22 can measure the EUV light 5 of substantially the same intensity as that of the EUV light 5 applied to the optical device 6. A method according to this embodiment is especially effective when the intensity of the plasma light source 11 is unstable.

For example, let I1 be the intensity of direct incident light detected by the sensor 22, and I2 be the intensity of scattered light from the optical device 6 detected by a sensor 10. If the reflectance R of the optical device 6 is defined to satisfy R=I2/I1, the reflectance of the optical device 6 can correctly be sensed regardless of the intensity of the plasma light source 11. For example, assume that the intensity of the plasma light source 11 varies by 5%. If the intensity I1 of the direct incident light is not measured, an error of 5% will occur in the reflectance. On the other hand, if the intensity I1 of the direct incident light is measured, no error will occur. Note that if the intensity I1 of the direct incident light is sufficiently stable, the arrangement according to the first embodiment of FIG. 1 will suffice.

Third Embodiment

Figure 3:
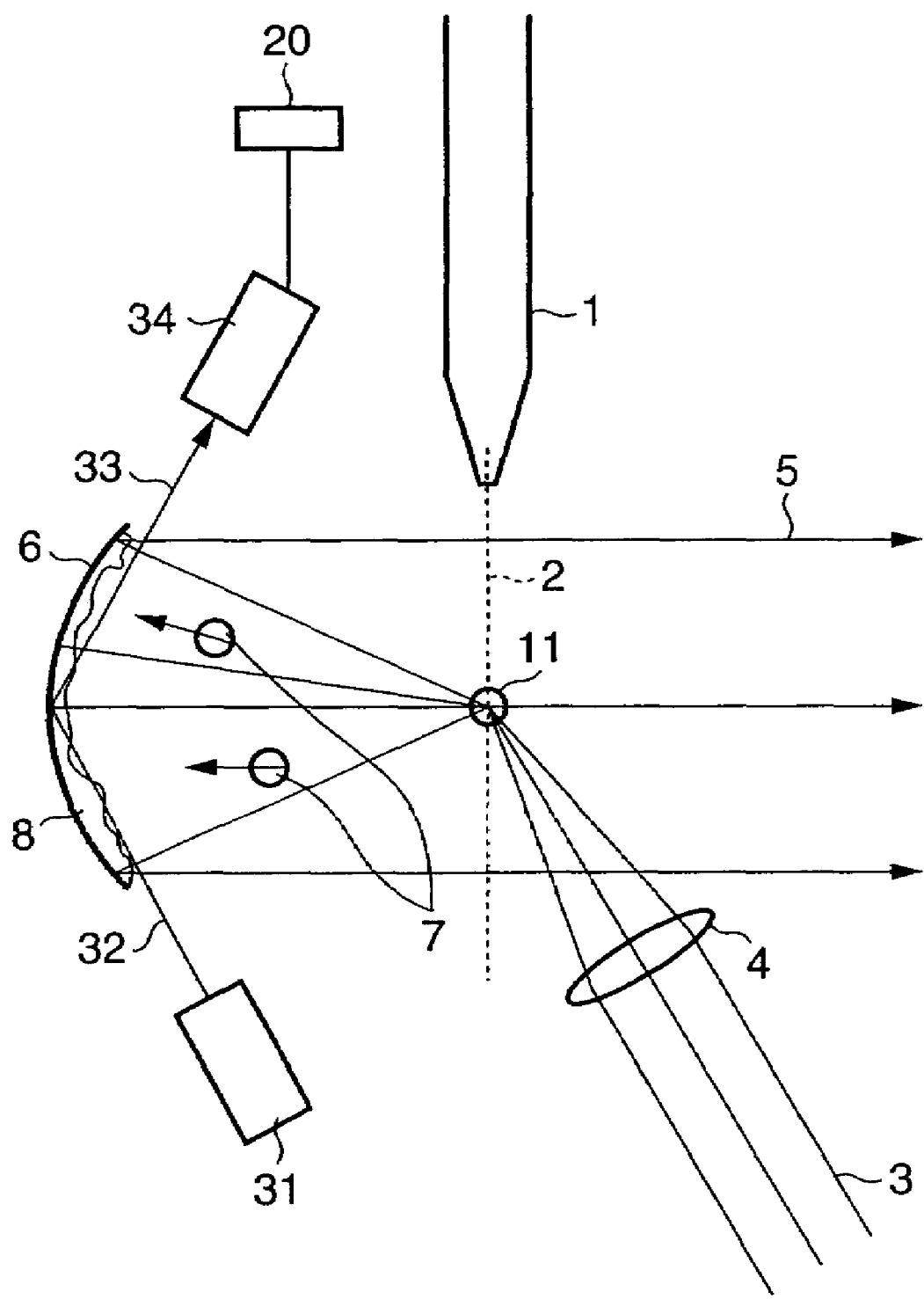
FIG. 3 is a schematic view showing an optical apparatus according to the third embodiment of the present invention.

FIG. 3 is a schematic view showing an optical apparatus according to the preferred third embodiment of the present invention. In FIG. 3, a sensor 34 is arranged outside the optical path of the EUV light 5 in place of the sensor 10 as the component in FIG. 1. A light source 31 is provided independently of a plasma light source 11. The optical device 6 is irradiated with light 32 from the light source 31, and the sensor 34 measures regularly reflected light 33 of the light 32. A measuring device 20 can measure an optical characteristic or its change of the optical device 6 on the basis of the measurement result of the regularly reflected light 33 obtained by the sensor 34.

Fourth Embodiment

Figure 4:
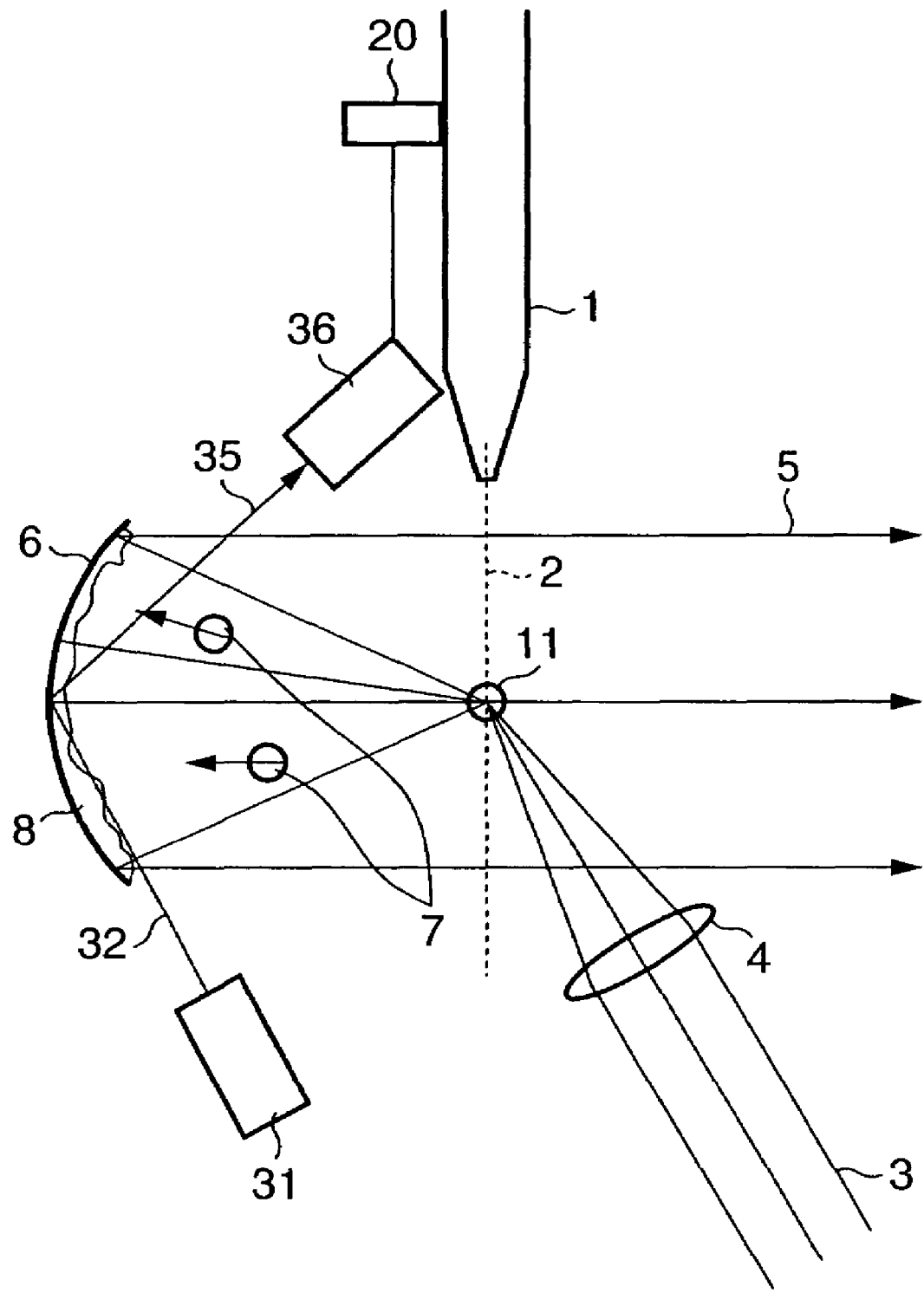
FIG. 4 is a schematic view showing an optical apparatus according to the fourth embodiment of the present invention.

FIG. 4 is a schematic view showing an optical apparatus according to the preferred fourth embodiment of the present invention. In FIG. 4, a sensor 36 is arranged outside the optical path of the EUV light 5 in place of the sensor 34 as the component in FIG. 3. The sensor 36 measures scattered light 35, which is generated when the optical device 6 is irradiated with light 32 emitted from another light source 31. A measuring device 20 measures an optical characteristic or its change of the optical device 6 on the basis of the detection result of the scattered light 35 obtained by the sensor 36. For example, if the amount of the debris 8 deposited on the surface of the optical device 6 increases, the amount of the scattered light 35 on the surface of the optical device 6 increases, thus changing the optical characteristic of the optical device 6. For this reason, the measuring device 20 can measure the optical characteristic or its change of the optical device 6 on the basis of the detection result of the scattered light 35.

Fifth Embodiment

Figure 5:
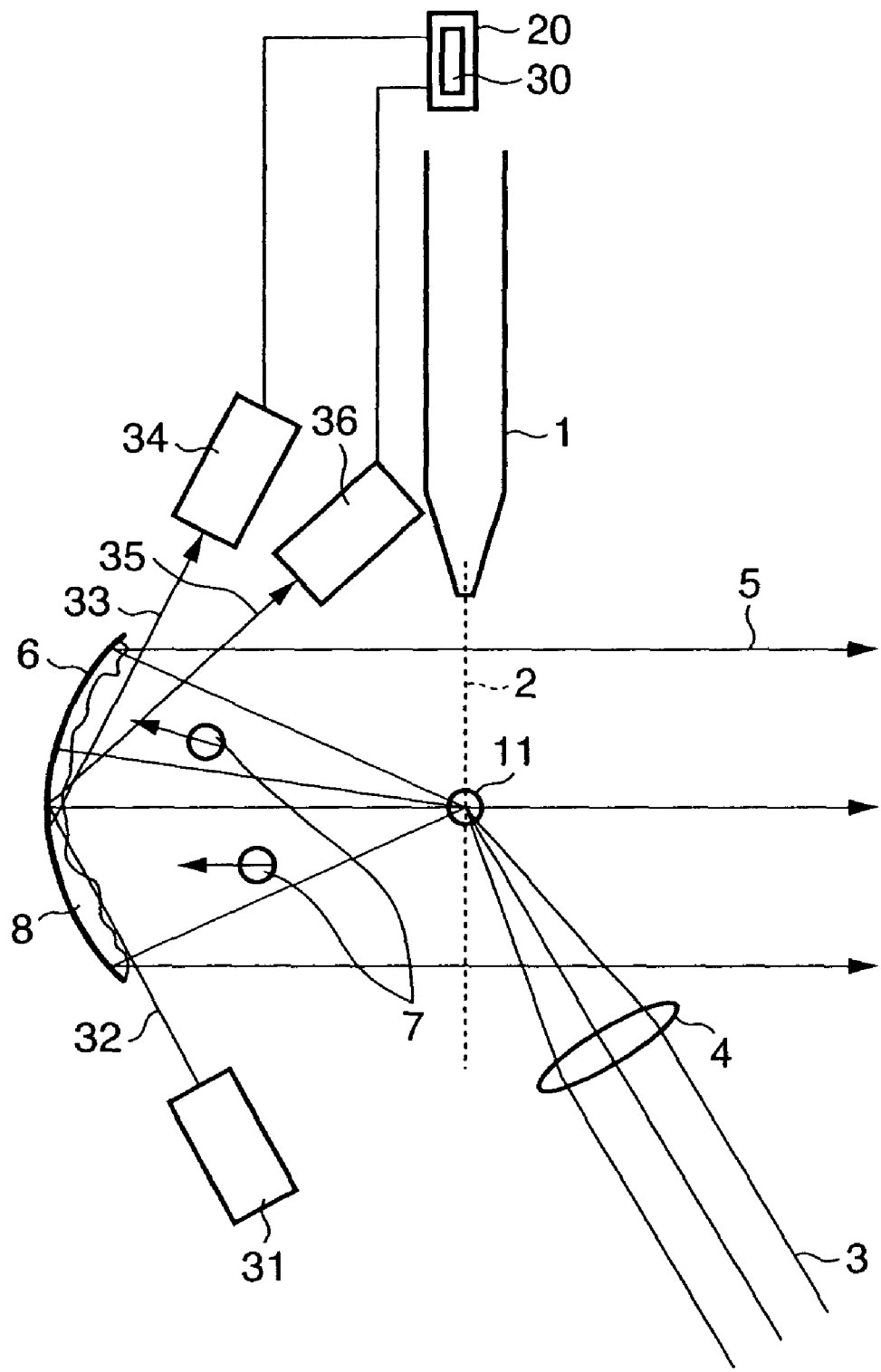
FIG. 5 is a schematic view showing an optical apparatus according to the fifth embodiment of the present invention.

FIG. 5 is a schematic view showing an optical apparatus according to the preferred fifth embodiment of the present invention. The optical apparatus in FIG. 5 has an optical sensor 34 as the component of FIG. 3 and an optical sensor 36 as the component of FIG. 4 arranged outside the optical path of the EUV light 5. The optical apparatus according to this embodiment further comprises a measuring device 20, which measures an optical characteristic or its change of the optical device 6 by comparing the detection result from the sensor 34 with that from the sensor 36. The measuring device 20 can measure the optical characteristic or its change of the optical device 6 on the basis of regularly reflected light 33 generated by the optical device 6 and scattered light 35 generated by the optical device 6.

A method according to this embodiment is especially effective when the intensity of another light source 31 is unstable. For example, let K1 be the output from the sensor 34, and K2 be the output from the sensor 36. If the relative intensity K is defined to satisfy K=K2/K1, the value of K becomes stable even when the output K1 varies. Accordingly, the magnitude of the scattered light 35 can correctly be detected.

Figure 6:
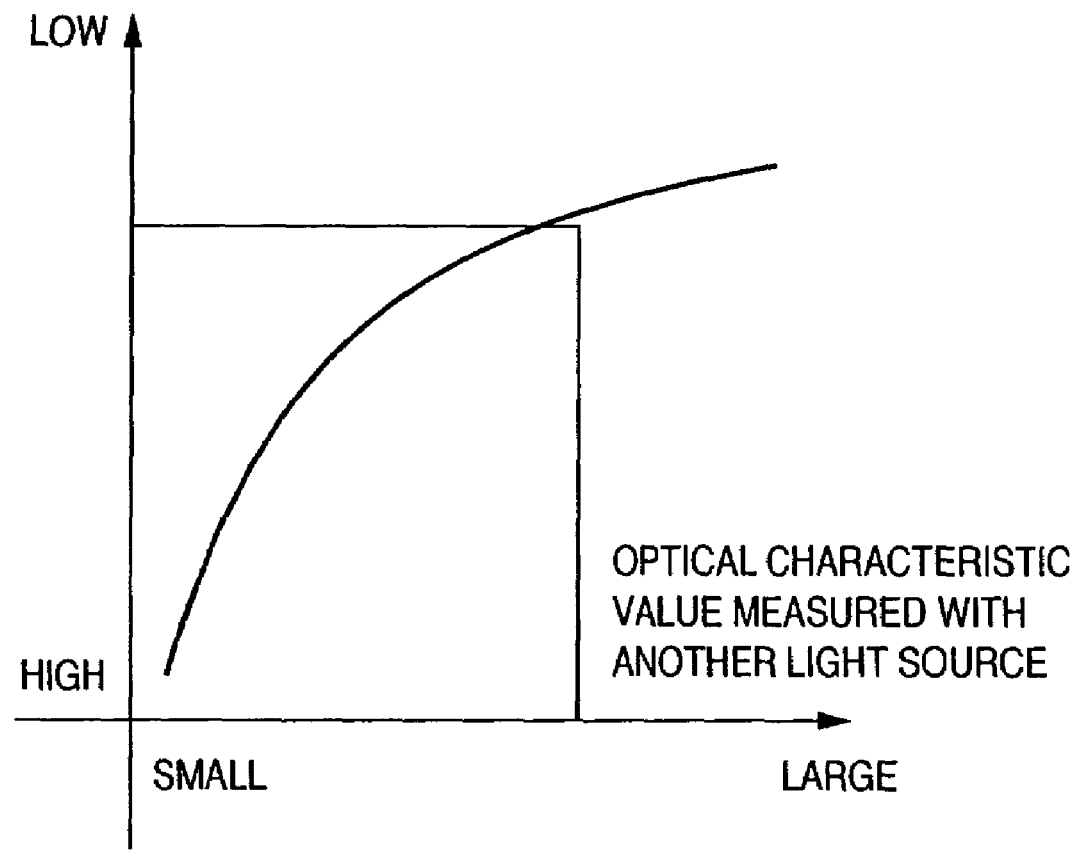
FIG. 6 is a schematic view showing the correlation between the change in optical characteristic of an optical device sensed with light from another light source and the change in optical characteristic of the optical device for EUV light emitted from a plasma light source.

FIG. 6 is a schematic view showing the correlation between the change in optical characteristic of the optical device 6 sensed with light from the other light source 31 and the change in optical characteristic of the optical device 6 for the EUV light 5 emitted from a plasma light source 11. In FIG. 6, the reflectance for the EUV light 5 is adopted as an example of the optical characteristics of the optical device 6.

As described above, the correlation between the reflectance of the optical device 6 for the EUV light 5 emitted from the plasma light source 11 and the change in optical characteristic of the optical device 6 sensed with light from the other light source 31 is obtained and stored in, e.g., a memory 30 in the measuring device 20. With this operation, the measuring device 20 can obtain the reflectance of the optical device 6 for the EUV light 5 from the value of the optical characteristic of the optical device 6 measured with the light from the other light source 31.

Sixth Embodiment

Figure 7:
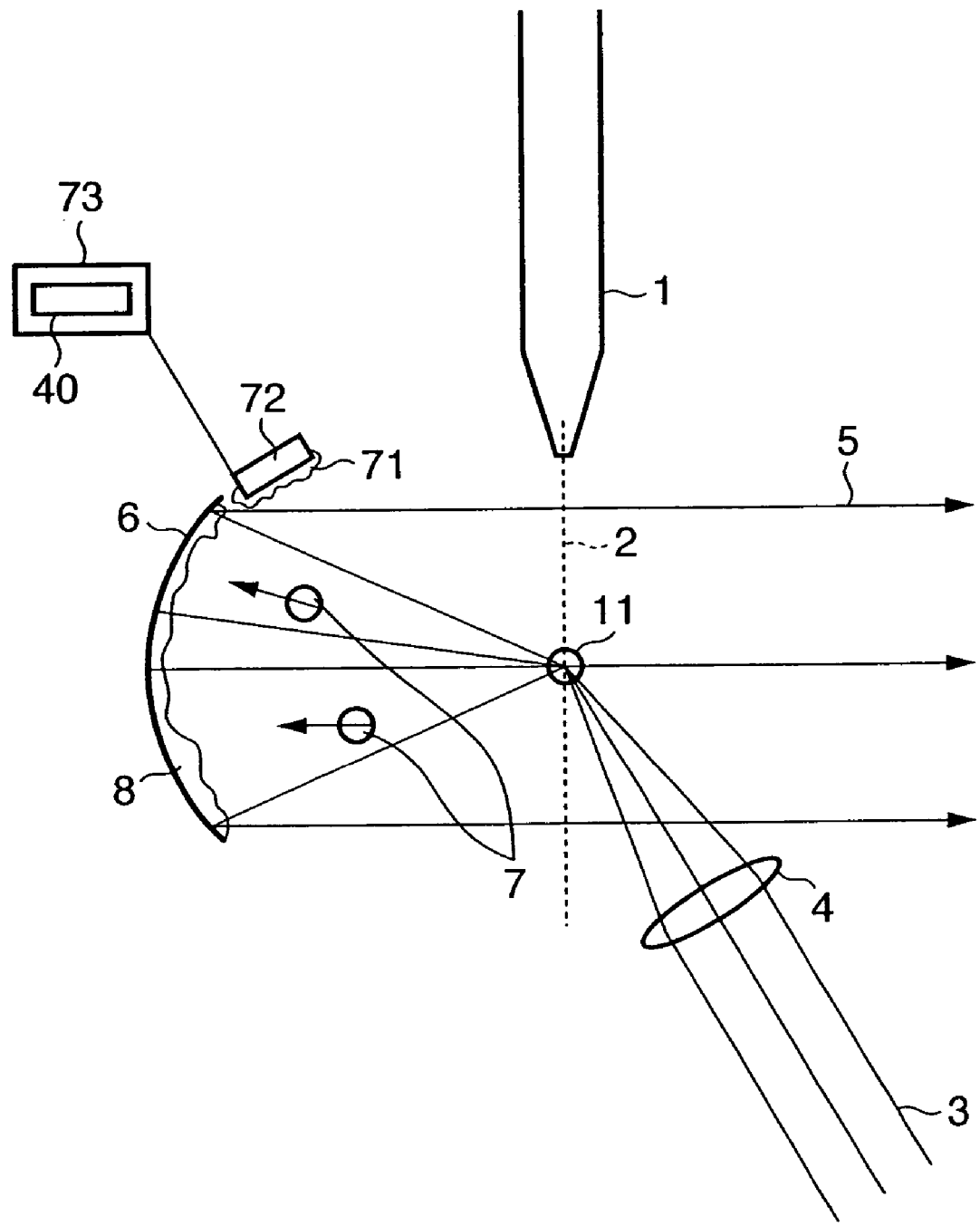
FIG. 7 is a schematic view showing an optical apparatus according to the sixth embodiment of the present invention.

FIG. 7 is a schematic view showing an optical apparatus according to the preferred sixth embodiment of the present invention. A deposition amount sensor 72 is arranged in the vicinity of the optical device 6 outside the optical path of the EUV light 5. The deposition amount sensor 72 comprises, e.g., a crystal oscillator and is designed such that its resonance frequency changes when debris 71 is deposited on the surface. A deposition amount measuring device 73 can sense the deposition amount of the debris 71 on the basis of the change amount of the resonance frequency of the deposition amount sensor 72.

Since the debris 7 generated from a plasma light source 11 scatters substantially uniformly and radially to the periphery of the light source 11, the amount of the debris 71 deposited on the deposition amount sensor 72 is substantially the same as that of the debris 8 deposited on the surface of the optical device 6. For this reason, the thickness of the debris 8 deposited on the optical device 6 can indirectly be sensed by sensing the debris 71 with the deposition amount measuring device 83.

Figure 8:
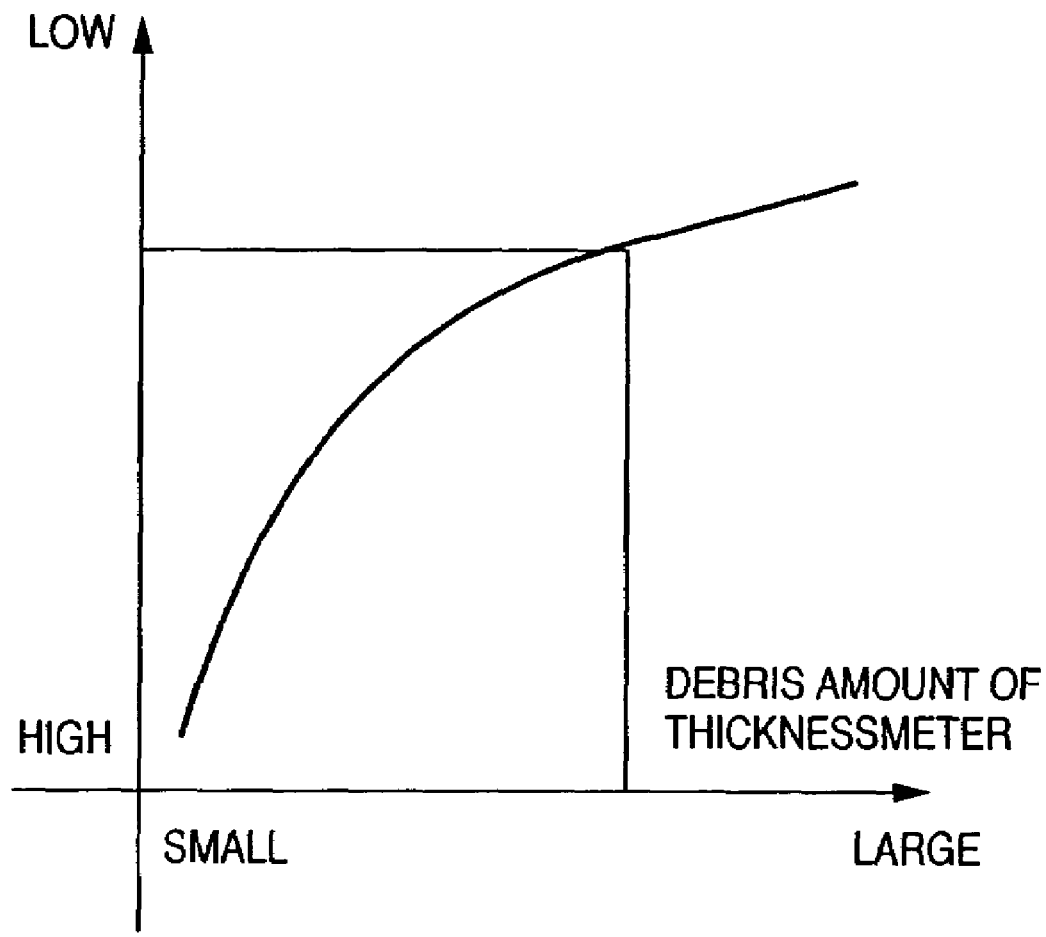
FIG. 8 is a schematic view showing the correlation between the deposition amount of debris deposited on a deposition amount sensor and the change in optical characteristic of an optical device.

FIG. 8 is a schematic view showing the correlation between the deposition amount of the debris 71 deposited on the deposition amount sensor 72 and the change in optical characteristic of the optical device 6. In FIG. 8, the reflectance of the optical device 6 for the EUV light 5 is adopted as an example of the optical characteristics.

As described above, the correlation between the deposition amount of the debris 71 on the deposition amount sensor 72 and the reflectance of the optical device 6 for the EUV light 5 is obtained and stored in, e.g., a memory 40 in the deposition amount measuring device 73. With this operation, the deposition amount measuring device 73 can obtain the optical characteristic or its change of the optical device 6 from the measurement result of the deposition amount sensor 72. For example, the deposition amount measuring device 73 can sense the deposition amount of the debris 71 on the deposition amount sensor 72 to calculate the reflectance of the optical device 6 for the EUV light 5.

Seventh Embodiment

Figure 9:
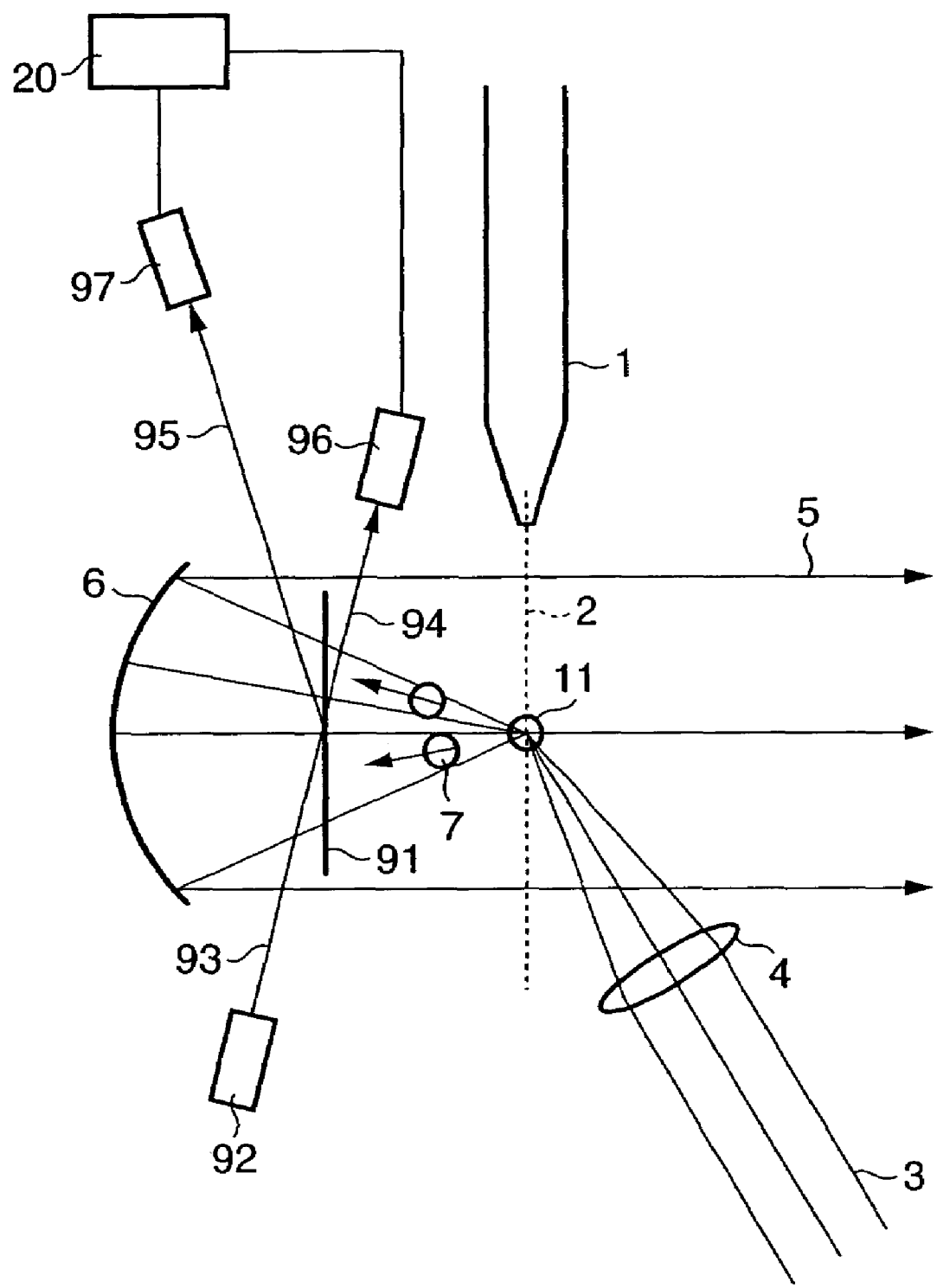
FIG. 9 is a schematic view showing an optical apparatus according to the seventh embodiment of the present invention.

FIG. 9 is a schematic view showing an optical apparatus according to the preferred seventh embodiment of the present invention. A filter 91 serving as a transmission optical device is arranged on the optical path in the vicinity of a plasma light source 11 to prevent the debris 7 from being deposited on the optical device 6. In FIG. 9, a sensor 96, which detects the magnitude of transmitted light 94, which is generated when light 93 emitted from another light source 92 passes through the filter 91, and a sensor 97, which detects scattered light 95, which is generated when the light 93 is scattered by the debris 7 deposited on the filter 91, are arranged outside the optical path of the EUV light 5. A measuring device 20 can measure an optical characteristic or its change of the filter 91 on the basis of the detection results of the sensors 96 and 92. If the deposition amount of the debris 7 on the filter 91 increases, the transmittance of the filter 91 for the EUV light 5 decreases. Along with this decrease, the magnitude of light detected by the sensor 97 increases.

For this reason, the measuring device 20 can calculate the transmittance of the filter 91 for the EUV light 5 from the output of the filter 91. In order to calculate the transmittance of the filter 91, the measuring device 20 may use the magnitude of the scattered light 96 from the other light source 92, the magnitude of the transmitted light 94, or a ratio F between the magnitude of the transmitted light 94 and that of the scattered light 95. For example, let F1 be the magnitude of the transmitted light 94, and F2 be the magnitude of the scattered light 95. In this case, F1, F2, or F, which is the ratio between them and defined to satisfy F=F2/F1, may be used.

As has been described, according to preferred embodiments of the present invention, an optical apparatus can measure in situ an optical characteristic or its change of an optical device even while it performs an operation such as exposure, or the like. Accordingly, the optical apparatus can sense the optical characteristic or its change of the optical device and the deposition amount of debris more correctly and quickly. For example, if an optical apparatus is employed as an exposure apparatus, which is designed such that optical devices can be replaced, the replacement timings of optical devices can more accurately and quickly be known. This prediction of the timing when optical devices need replacing can shorten the downtime of the apparatus and reduce the cost of the entire apparatus. In the present invention, an optical device, an optical characteristic or its change of which are to be measured or monitored in situ, may comprise a reflection optical device as described in, e.g., the first to sixth embodiments or a transmission optical device as described in, e.g., the seventh embodiment. According to the preferred embodiments of the present invention, another experimental system may be prepared. The correlation between the reflectance of an optical device for EUV light emitted from a predetermined light source in the experimental system and an optical characteristic of the optical device sensed with light from another light source or its change, or the deposition amount of debris on the optical device may be calculated in advance. The experimental result may be stored in, e.g., a memory in a measuring device.

In the above embodiments, another light source 31 and 92 may include a light source emitting a light with a wavelength equal to the wavelength of the EUV light 5 (exposure light) or a light source emitting light with a wavelength different from the wavelength of EUV light 5, e.g., a semiconductor laser such as a He—Ne laser.

In the above embodiments, an EUV exposure apparatus as an example of an optical apparatus has been described. However, the present invention is not limited to this. An optical apparatus according to a preferred embodiment of the present invention is applicable to an optical apparatus which uses a light source whose wavelength is longer than that of an EUV exposure apparatus. In this case, a filter, lens, or the like, may be adopted as a transmission optical device.

OTHER EMBODIMENT

Figure 12:
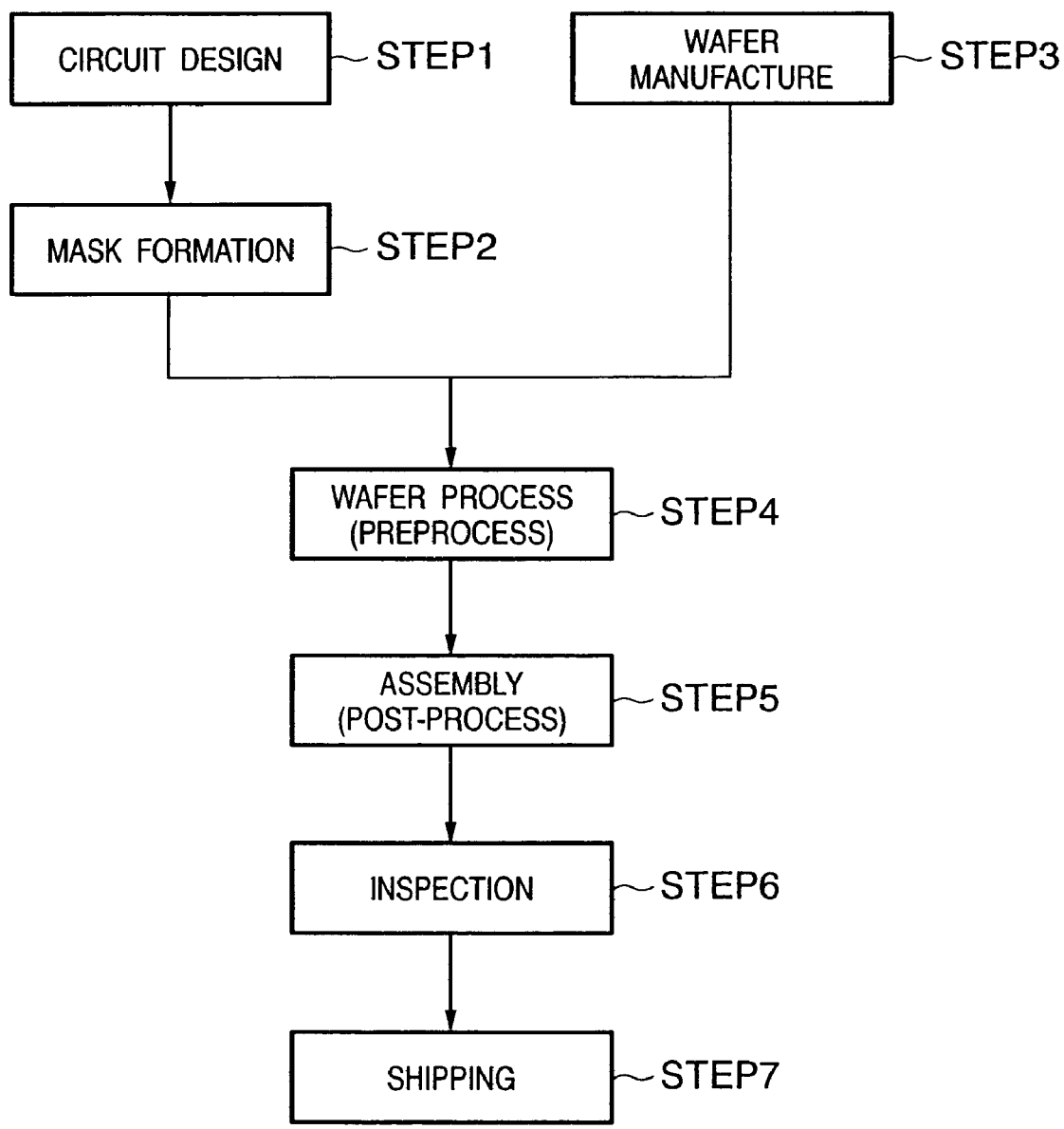
FIG. 12 is a flow chart showing the flow of the whole manufacturing process of a semiconductor device.

The manufacturing process of a semiconductor device using the above-mentioned optical apparatus will be described next. FIG. 12 shows the flow of the whole manufacturing process of the semiconductor device. In step 1 (circuit design), a semiconductor device circuit is designed. In step 2 (mask formation), a mask having the designed circuit pattern is formed. In step 3 (wafer manufacture), a wafer is manufactured by using a material such as silicon. In step 4 (wafer process), called a preprocess, an actual circuit is formed on the wafer by lithography using the prepared mask and wafer. Step 5 (assembly), called a post-process, is the step of forming a semiconductor chip by using the wafer formed in step 4, and includes an assembly process (dicing and bonding) and a packaging process (chip encapsulation). In step 6 (inspection), the semiconductor device manufactured in step 5 undergoes inspections such as an operation confirmation test and a durability test. After these steps, the semiconductor device is completed and shipped (step 7).

Figure 13:
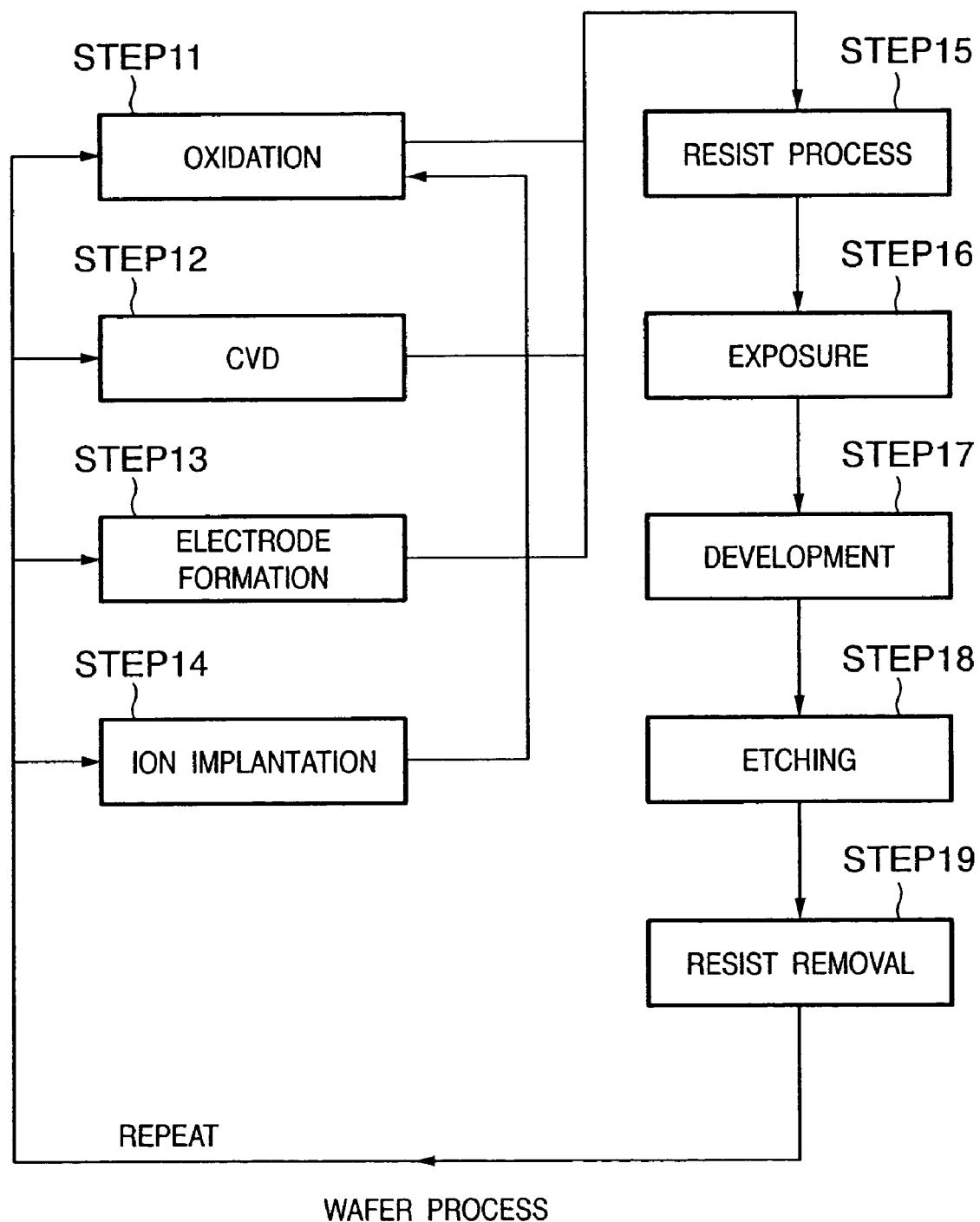
FIG. 13 is a flow chart showing the detailed flow of the wafer process.

FIG. 13 shows the detailed flow of the above-mentioned wafer process. In step 11 (oxidation), the wafer surface is oxidized. In step 12 (CVD), an insulating film is formed on the wafer surface. In step 13 (electrode formation), an electrode is formed on the wafer by vapor deposition. In step 14 (ion implantation), ions are implanted in the wafer. In step 15 (resist processing), a photosensitive agent is applied to the wafer. In step 16 (exposure), the circuit pattern is transferred onto the wafer using the above-mentioned optical apparatus. In step 17 (development), the exposed wafer is developed. In step 18 (etching), the resist is etched, except for the developed resist image. In step 19 (resist removal), an unnecessary resist after etching is removed. These steps are repeated to form multiple circuit patterns on the wafer.

According to the present invention, an optical characteristic or its change of an optical device arranged on an optical path can be measured in situ.

As many apparently widely different embodiments of the present invention can be made without departing from the spirit and scope thereof, it is to be understood that the invention is not limited to the specific embodiments thereof except as defined in the claims.

The invention claimed is:

1. An optical apparatus comprising:
    an optical device arranged on an optical path extending from a light source to a predetermined position;
    an optical sensor; and
    a measuring device which measures an optical characteristic or a change in an optical characteristic of said optical device on the basis of an output from said optical sensor,
    wherein said optical sensor is arranged outside the optical path and senses light which is emitted from a second light source arranged outside the optical path and is reflected by said optical device.

2. The apparatus according to claim 1, wherein said apparatus further comprises a second light sensor arranged outside the optical path to sense light,
    the second optical sensor senses light which is emitted from the second light source and is scattered by said optical device, and
    said measuring device measures the optical characteristic or the change in the optical characteristic of said optical device on the basis of an output from the second optical sensor in addition to the output from said optical sensor.

3. The apparatus according to claim 1, wherein said apparatus further comprises a memory which stores information indicating a correlation between the optical characteristic or the change in optical characteristic of said optical device and a detection or measurement result of light which is emitted from the second light source and is reflected by said optical device, and
    said measuring device measures the optical characteristic or the change in optical characteristic of said optical device on the basis of the output from said optical sensor and the correlation.

4. The apparatus according to claim 2, wherein said apparatus further comprises a memory which stores information indicating a correlation between the optical characteristic or the change in optical characteristic of said optical device and a detection or measurement result of light which is emitted from the second light source and is scattered by said optical device, and
said measuring device measures the optical characteristic or the change in optical characteristic of said optical device on the basis of the output from the second optical sensor and the correlation.

5. The apparatus according to claim 1, wherein the light source comprises an EUV light source.

6. The apparatus according to claim 1, wherein the optical characteristic is reflectance.

7. The apparatus according to claim 1, wherein said apparatus further comprises a projection optical system for projecting a pattern onto a substrate and is configured as an exposure apparatus.

8. A semiconductor device manufacturing method comprising steps of:
coating a substrate with a photosensitive agent;
transferring a pattern onto the substrate coated with the photosensitive agent in said coating step using the apparatus as defined in claim 7; and
developing the photosensitive agent on the substrate bearing the pattern transferred in the exposure step.

9. An optical apparatus comprising:
an optical device arranged on an optical path extending from a light source to a predetermined position;
an optical sensor; and
a measuring device which measures an optical characteristic or a change in an optical characteristic of said optical device on the basis of an output from said optical sensor,
wherein said optical sensor is arranged outside the optical path and senses light which is emitted from a second light source arranged outside the optical path and is scattered by said optical device.

10. The apparatus according to claim 9, wherein said apparatus further comprises a second light sensor arranged outside the optical path to sense light,
the second optical sensor senses light which is emitted from the second light source and passes through said optical device, and
said measuring device measures the optical characteristic or the change in optical characteristic of said optical device on the basis of an output from the second optical sensor in addition to the output from said optical sensor.

11. The apparatus according to claim 9, wherein the light source comprises an EUV light source.

12. The apparatus according to claim 9, wherein the optical characteristic is reflectance.

13. The apparatus according to claim 9, wherein said apparatus further comprises a projection optical system for projecting a pattern onto a substrate and is configured as an exposure apparatus.

14. A semiconductor device manufacturing method comprising steps of:
coating a substrate with a photosensitive agent;
transferring a pattern onto the substrate coated with the photosensitive agent in said coating step using an optical apparatus as defined in claim 13; and
developing the photosensitive agent on the substrate bearing the pattern transferred in the exposure step.

15. An optical apparatus comprising:
an optical device arranged on an optical path extending from a light source to a predetermined position;
an optical sensor; and
a measuring device which measures an optical characteristic or a change in an optical characteristic of said optical device on the basis of an output from said optical sensor,
wherein said optical sensor is arranged outside the optical path and senses light which is emitted from a second light source arranged outside said optical path and is scattered by a substance generated from the light source and deposited on said optical device.

16. The apparatus according to claim 15, wherein the light source comprises an EUV light source.

17. The apparatus according to claim 15, wherein the optical characteristic is reflectance.

18. The apparatus according to claim 15, wherein said apparatus further comprises a projection optical system for projecting a pattern onto a substrate and is configured as an exposure apparatus.

19. A semiconductor device manufacturing method comprising steps of:
coating a substrate with a photosensitive agent;
transferring a pattern onto the substrate coated with the photosensitive agent in said coating step using an optical apparatus as defined in claim 18; and
developing the photosensitive agent on the substrate bearing the pattern transferred in the exposure step.

20. An optical apparatus comprising:
an optical device arranged on an optical path extending from a light source to a predetermined position;
a deposition amount sensor; and
a measuring device which measures a deposition amount of a substance generated from the light source and deposited on the optical device on the basis of an output from the deposition amount sensor,
wherein the deposition amount sensor is arranged outside the optical path.

21. The apparatus according to claim 20, wherein said apparatus further comprises:
a memory which stores information indicating a correlation between the optical characteristic or the change in optical characteristic of said optical device and the deposition amount of the substance deposited on said optical device, and
said measuring device derives the optical characteristic or the change in optical characteristic of said optical device on the basis of an output from the deposition amount sensor and the correlation.

22. The apparatus according to claim 20, wherein said apparatus further comprises a projection optical system for projecting a pattern onto a substrate and is configured as an exposure apparatus.

23. A semiconductor device manufacturing method comprising steps of:
coating a substrate with a photosensitive agent;
transferring a pattern onto the substrate coated with the photosensitive agent in said coating step using an optical apparatus as defined in claim 22; and
developing the photosensitive agent on the substrate bearing the pattern transferred in the exposure step.

24. An optical apparatus comprising:
an optical device arranged on an optical path extending from a light source to a predetermined position;
an optical sensor; and a measuring device which measures an optical characteristic or a change in an optical characteristic of said optical device on the basis of an output from said optical sensor, wherein said optical sensor is arranged outside the optical path and senses light which is emitted from a second light source arranged outside said optical path and passes through said optical device.

25. The apparatus according to claim 24, wherein said apparatus further comprises a projection optical system for projecting a pattern onto a substrate and is configured as an exposure apparatus.

* * * * *